United States Patent [19]

Mattison et al.

[11] Patent Number: 5,785,672
[45] Date of Patent: Jul. 28, 1998

[54] LUMBOSACRAL SUPPORT BELTS AND METHOD

[75] Inventors: Philip H. Mattison; Douglas W. Mattison, both of Forest Lake, Minn.

[73] Assignee: Core Products International, Inc., Osceola, Wis.

[21] Appl. No.: 859,071

[22] Filed: May 20, 1997

[51] Int. Cl.$^6$ ......................................... A61F 5/00
[52] U.S. Cl. .................. 602/19; 128/99.1; 128/101.1; 450/155
[58] Field of Search ................... 602/19; 2/44, 92; 128/96.1, 99.1, 100.1, 101.1; 450/15, 155

[56] References Cited

U.S. PATENT DOCUMENTS

| | | |
|---|---|---|
| D. 325,683 | 4/1992 | Meyer et al. ................ D6/601 |
| 4,175,553 | 11/1979 | Rosenberg . |
| 4,572,167 | 2/1986 | Brunswick . |
| 4,627,109 | 12/1986 | Carabelli et al. . |
| 4,833,730 | 5/1989 | Nelson . |
| 4,836,194 | 6/1989 | Sebastian et al. . |
| 5,040,524 | 8/1991 | Votel et al. . |
| 5,070,866 | 12/1991 | Alexander et al. . |
| 5,148,549 | 9/1992 | Sydor . |
| 5,241,704 | 9/1993 | Sydor . |
| 5,536,246 | 7/1996 | Saunders . |

*Primary Examiner*—Linda C. Dvorak
*Attorney, Agent, or Firm*—Nawrocki, Rooney & Sivertson, P.A.

[57] ABSTRACT

A lumbosacral support belt, a series of lumbosacral support belts, and a method of fitting lumbosacral support belts which are manufactured with specific relationships of certain dimensions so that a minimum inventory of belts fits a large percentage of the wearer population. In particular the hip to waist differential and the total waist measurement determine the height of the belt, the dimensions of the back panel and the length of the adjustable support straps.

17 Claims, 3 Drawing Sheets

1

LUMBOSACRAL SUPPORT BELTS AND METHOD

BACKGROUND OF THE INVENTION

This invention relates generally to orthopedic lumbosacral supports and more particularly to lumbosacral supports manufactured with a specific geometrical shape which provides for the optimized fitting of different wearer body types or sizes using a minimum inventory of supports and employing an inventive fitting method.

While lumbosacral support belts are known, current designs require a large number of belts to accommodate differing wearer body types. This either limits the number of individuals that can be fitted without special order or requires a large inventory. In addition, current fitting techniques do not adequately take into account relationships of the body for optimum fit.

SUMMARY OF THE INVENTION

The present invention provides a series of lumbosacral support belts for wearers having a range of body sizes wherein a minimum of standard sizes will accommodate most wearers.

It is an object of the present invention to provide a series of improved orthopedic devices for protecting and supporting a body portion wherein the device comprises a trapezoidal back panel having parallel top and bottom edges and first and second side panels extending from side edges thereof, wherein each of the devices in the series has a total length $L_{total}$ and each device includes a back panel comprising a resilient stretchable material with support members attached thereto for stiffening selected regions of the panel, said back panel having a length along its top edge of $L_{top}$ and having a length along its bottom edge of $L_{bottom}$ that is a selected percentage of the total length $L_{total}$ of the device, said back panel having a height H between its bottom edge and its top edge wherein H in inches is equal to a fixed minimum width plus a distance substantially equal to the difference between $L_{bottom}$ and $L_{top}$ multiplied by a fixed multiplier where the multiplier is the same for each of the devices in the series; and also including first and second side panels, each of which is attached at one end thereof to a side edge of the back panel, the other end of each of said side panels also comprising fastening means for securing the device with the support members of the back panel supporting the lumbosacral area of the wearer with the top edge of the back panel adjacent the waist of the wearer and the lower edge of the back portion adjacent to the hips of the wearer.

The object above can be attained by provision of an improved orthopedic device for protecting and supporting a body portion wherein the device comprises a trapezoidal back panel having parallel top and bottom edges and first and second side panels extending from the side edges thereof, wherein the device has a total length $L_{total}$ and includes a back panel comprising a resilient stretchable material with support members attached thereto for stiffening selected regions of the panel, said back panel having a length along its top edge of $L_{top}$ and a length along its bottom edge of $L_{bottom}$ that is approximately one third the length of the total length $L_{total}$ of the support, said back panel having a height H between its bottom edge and its top edge wherein H, in inches, is equal to approximately 4+2 ($L_{bottom}-L_{top}$); and also includes first and second side panels, each of which is attached at one end thereof to a side edge of the back panel, the other end of each of said side panels also comprising fastening means for securing the device with the support members of the back panel supporting the lumbosacral area of the wearer with the top edge of the back panel adjacent the waist of the wearer and the lower edge of the back portion adjacent to the hips of the wearer.

It is a still further object of the invention to provide a method for fitting lumbosacral belts to a wearer comprising the steps of measuring the circumference of the waist of the wearer; measuring the circumference of the hips of the wearer; and selecting a belt from an inventory of belts manufactured in varying sizes as described above where the selected belt has a hip to waist differential closest to the measured hip to waist differential of the wearer.

DETAILED DESCRIPTION OF THE PREFERRED EMBODIMENT

Figure 1:
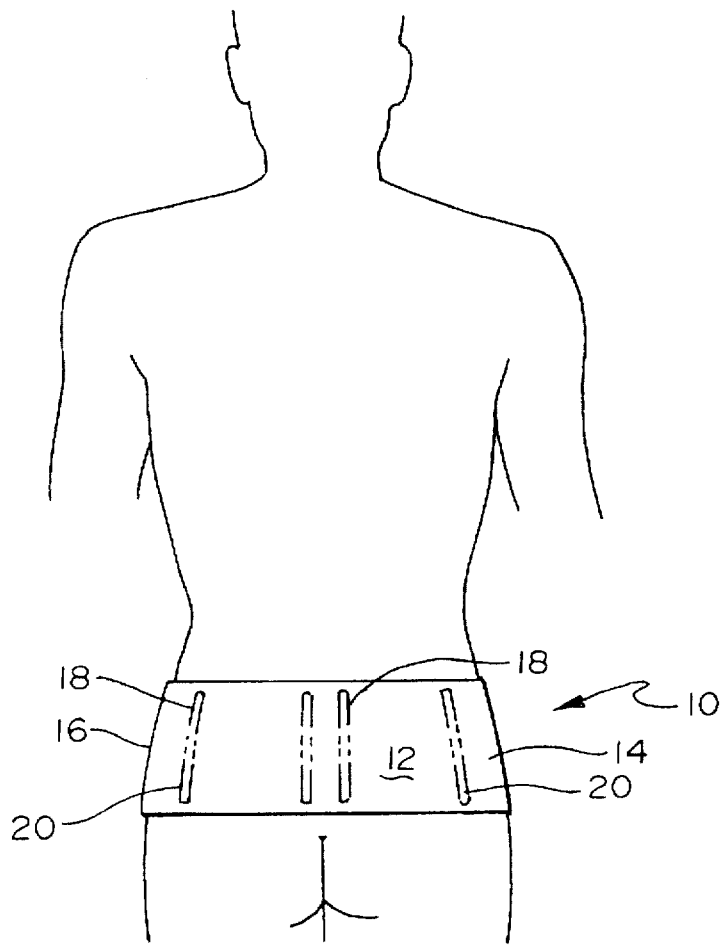
FIG. 1 is a back perspective view of the preferred lumbosacral back support system of the present invention illustrated as it would be operatively positioned on the human body.

An orthopedic device 10 in accordance with the present invention is shown in FIG. 1 as it is positioned on a human body to support the lumbosacral region consisting of the five lumbar vertebrae and the sacrum. Specifically, device 10 in the embodiment shown is a belt or brace or support which is comprised of a trapezoidal back panel 12 and first and second side panels 14 and 16. Spinous stays 18 are support members attached to back panel 12. Additional support members in the form of lateral stays 20 are positioned as seen in FIGS. 1 or 2 at the side edges of back panel 12.

Figure 2:
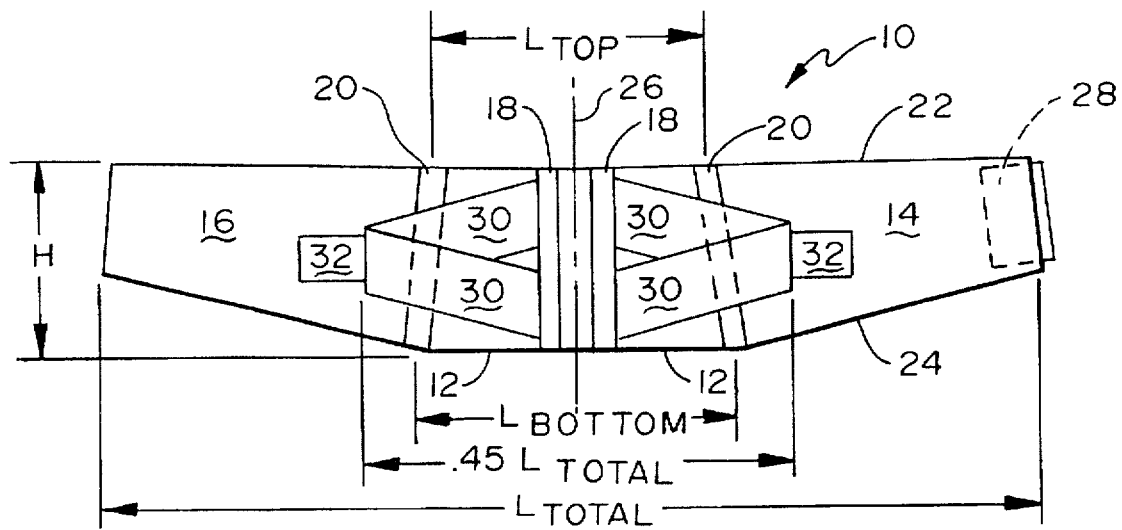
FIG. 2 is a plan view of a back support device as shown in FIG. 1.

FIG. 2 shows device 10 opened flat with the top edge 22 corresponding to the portion which is adjacent to the wearer's waist and the bottom edge 24 corresponding to the portion which is adjacent to the wearer's hips. Spinous members or stays 18 are shown as oriented parallel to the vertical midline 26 of back panel 12. Spinous stays 18 are displaced from vertical midline 26 by a distance sufficient to place them closely adjacent to the spine but not in contact with it when the device is worn by the wearer as shown in FIG. 1. Stays 18 are placed 1.25 inches on center from the midpoint of device 12. In the preferred embodiment shown, the gap between the inside edges of the spinous stays is approximately 1.5 inches. Although most of the measurements of devices 10 may vary considerably in the various size configurations of the series of orthopedic devices, the separation of the spinous stays remains at the same distance throughout the series of varying size belts because the distance necessary to keep the stays from directly contacting the spine is essentially the same over the entire range in sizes.

In the embodiments shown herein back panel 12 is formed of a suitable stretchable fabric such as 100% stretch elastic or a stretchable Spandex material. Side panels 14 and 16 are made from loop fabrics while fastening means or hook material 28 is attached on the outside of left side panel 14 so that device 12 is closed by pulling right side panel 16 over left side panel 14 so that hook material 28 engages the loops on the outside surface of left side panel 14. The loop material of side panels 14 and 16 and hook material 28 may be of any type well known in the industry which would form a hook type fastener such as Velcro (registered trademark) brand. The loop materials are relatively non-stretchable.

In order to provide an adjustable additional tension on the supported portion of the back, adjustable support straps 30 are provided. One end of support straps 30 is anchored adjacent to spinous stays 18 while the other end is connected to a Velcro hook closure 32 which has the operable side facing side panels 14 or 24 for engagement therewith at selected locations in accordance with wearer preference and comfort. In the preferred embodiment shown, support strap hook closures 32 are 3.5 inches in length with 2.75 inches thereof overlapping side panels 14 and 16 as a guard against peeling. Closures 32 are centered on the ends of elastic panels 14 and 16.

As shown in FIG. 2, there are two support straps on each side of the centerline of device 10. The total span of support straps 30 is proportionately varied for the various supports in the inventory of supports necessary to fit an optimal percentage of the wearer population. In accordance with the present invention, the total length of the unstretched support straps 32 is approximately 0.45 times the total length $L_{total}$ of device 10.

Figure 3:
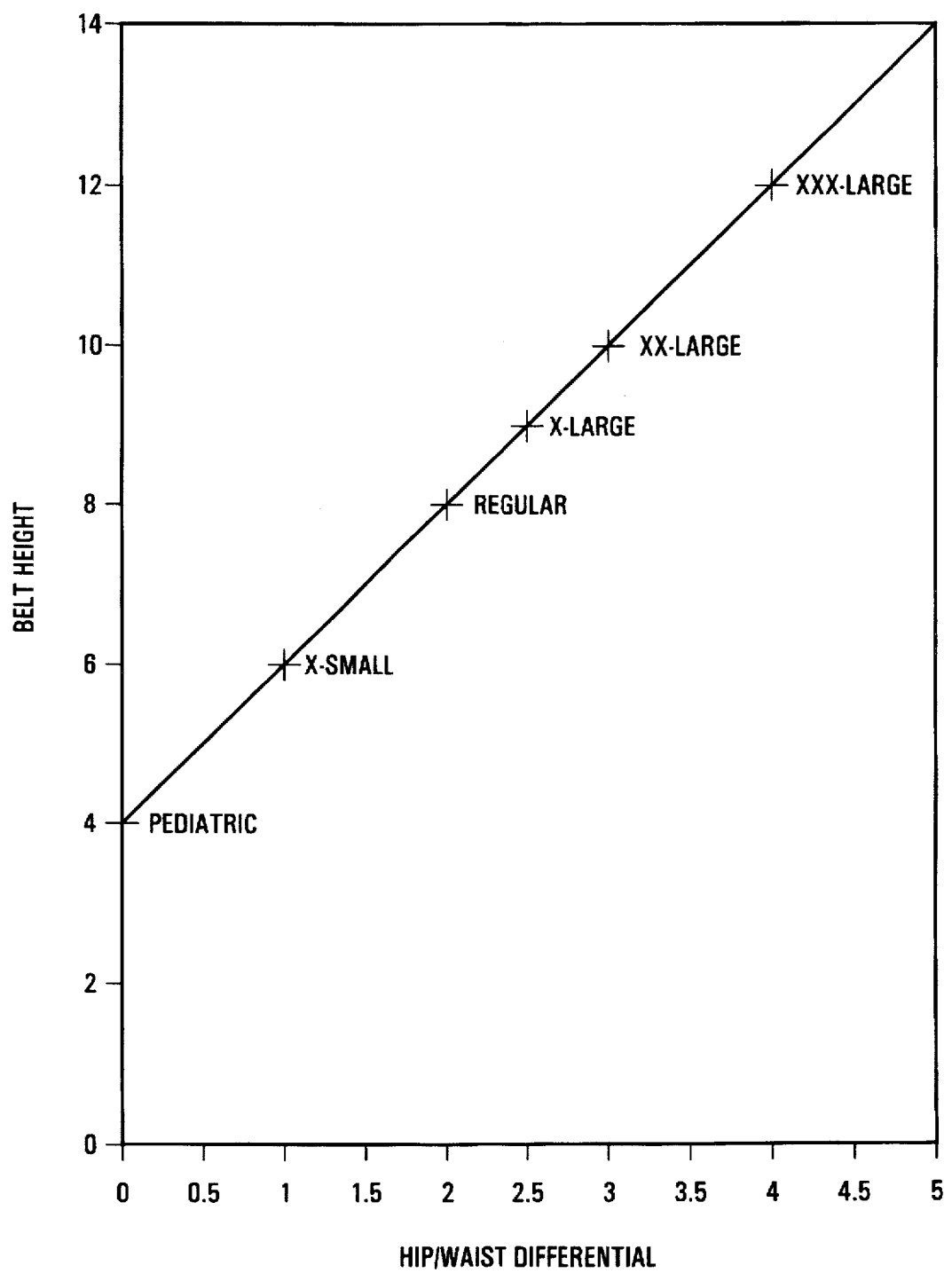
FIG. 3 is a graph showing the relationship between the height of the back panel of a support belt and the differential between the hip and waist circumferential measurements.
Figure 4:
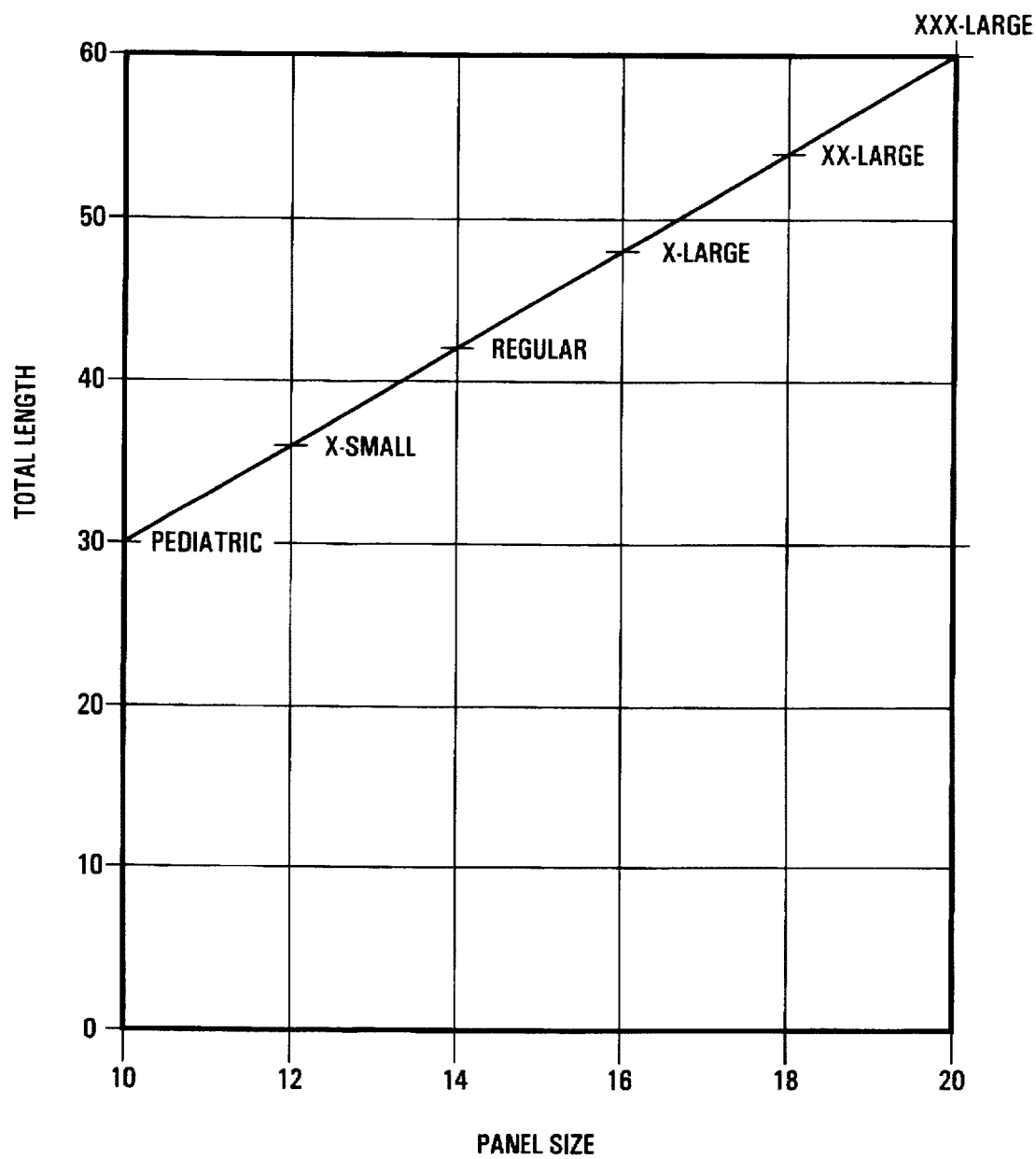
FIG. 4 is a graph showing the relationship between the width of the back panel of a support belt and the total length of the support belt.

In accordance with the present invention it can be seen that a series of belts may be manufactured in varying sizes using the dimensional relationships outlined above. For example a series of belts might include the six sizes listed on the graphs of FIGS. 3 and 4. It has been determined that belts manufactured in the sizes indicated will be suitable for a very high percentage of the potential wearer population.

In order to fit a potential wearer to a belt in a series of belts manufactured in accordance with the present invention, the waist and hip circumference of the wearer would be measured and the hip to waist differential would be calculated. The suitable belt would be determined by selecting a belt within the series having a hip to waist differential closest to the measured hip to waist differential.

Since the hip to waist differential determines the length of the belt, the height and the length of the support straps, there is no need to provide multiple belts in each waist size with varying belt widths as has been previously necessary using conventional belt fitting and sizing methods.

Although the present invention has been described in terms of the presently preferred embodiment, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A series of improved orthopedic devices for protecting and supporting a body portion wherein the device comprises a trapezoidal back panel having parallel top and bottom edges and first and second side panels extending from the side edges thereof, wherein each of the devices in the series has a total length $L_{total}$ and comprises:

a. a back panel comprising a resilient stretchable material with support members attached thereto for stiffening selected regions of the panel, said back panel having a length along its top edge of $L_{top}$ and a length along its bottom edge of $L_{bottom}$ that is a selected percentage of the total length $L_{total}$ of the device, said back panel having a height H between its bottom edge and its top edge wherein H in inches is equal to a fixed minimum width plus a distance substantially equal to the difference between $L_{bottom}$ and $L_{top}$ multiplied by a fixed multiplier where the multiplier is the same for each of the devices in the series; and b. first and second side panels, each of which is attached at one end thereof to a side edge of the back panel, the other end of each of said side panels also comprising fastening means for securing the device with the support members of the back panel supporting the lumbosacral area of the wearer with the top edge of the back panel adjacent the waist of the wearer and the lower edge of the back portion adjacent to the hips of the wearer.

2. A method for fitting lumbosacral belts to a wearer comprising the steps of:

a. measuring the circumference of the waist of the wearer;

b. measuring the circumference of the hips of the wearer;

c. determining the hip to waist differential of the wearer; and d. selecting a belt from an inventory of belts manufactured in varying sizes according to claim 1 where the selected belt has a hip to waist differential closest to the determined hip to waist differential of the wearer.

3. An improved orthopedic device for protecting and supporting a body portion wherein the device comprises a trapezoidal back panel having parallel top and bottom edges and first and second side panels extending from the side edges thereof, wherein the device has a total length $L_{total}$ and comprises:

a. a back panel comprising a resilient stretchable material with support members attached thereto for stiffening selected regions of the panel, said back panel having a length along its top edge of $L_{top}$ and a length along its bottom edge of $L_{bottom}$ that is approximately one third the length of the total length $L_{total}$ of the support, said back panel having a height H between its bottom edge and its top edge wherein H in inches is equal to approximately $4+2(L_{bottom}-L_{top})$; and b. first and second side panels, each of which is attached at one end thereof to a side edge of the back panel, the other end of each of said side panels also comprising fastening means for securing the device with the support members of the back panel supporting the lumbosacral area of the wearer with the top edge of the back panel adjacent the waist of the wearer and the lower edge of the back portion adjacent to the hips of the wearer.

4. The invention of claim 3, wherein the support members comprise a pair of spinous stays oriented parallel to a vertical midline of the back panel and displaced therefrom a distance sufficient to place them closely adjacent to the spine but not in contact with it when the device is worn by the wearer.

5. The invention of claim 4, wherein the separation between the inside edges of the spinous stays is approximately 1.5 inches.

6. The invention of claim 4, wherein adjustable support straps of elastic material are attached at one end to the back panel adjacent the spinous stays and the other end of which includes fastening means for fastening the other end of said support straps to a desired position on one of the side panels to increase the amount of support provided.

7. The invention of claim 6, wherein support straps are attached to both of the side panels and the total length of the support straps from one fastening means to the other when the support straps are positioned with the support straps unstressed is approximately 0.45 of the total length $L_{total}$.

8. The invention claimed in claim 3, wherein the support means also comprises lateral stays, one each of which is positioned at the side edges of the back panel.

9. The invention of claim 3, where the side panels are made from loop material and the side panel fastening means comprise hook material for engaging the loop material and securing the end of one of the side panels to the outer surface of the other side panel.

10. The invention of claim 9, where the fastening means of the adjustable support straps comprise hook means at the end of the adjustable support straps for engaging the loop material of the side panels.

11. The invention of claim 3, where the height of the side panels is tapered from the height of the back panel at the end of the strap adjacent the side edge of the back panel to a minimum height of about four and a half inches.

12. The invention of claim 3, for pediatric sizes in which $L_{total}$ is about 30 inches and $L_{bottom}$ and $L_{top}$ are each about 10 inches.

13. The invention of claim 3, for extra small sized wearers where $L_{total}$ is about 36 inches and $L_{top}$ is about 1 inch less than $L_{bottom}$.

14. The invention of claim 3, for regular sized wearers where $L_{total}$ is about 42 inches and $L_{top}$ is about 2 inches less than $L_{bottom}$.

15. The invention of claim 3, for extra large sized wearers where $L_{total}$ is about 48 inches and $L_{top}$ is about 2½ inches less than $L_{bottom}$.

16. The invention of claim 3, for extra extra large sized wearers where $L_{total}$ is about 54 inches and $L_{top}$ is about 3 inches less than $L_{bottom}$.

17. The invention of claim 3, for extra extra extra large sized wearers where $L_{total}$ is about 60 inches and $L_{top}$ is about 4 inches less than $L_{bottom}$.

* * * * *